(12) United States Patent
Swerdlow

(10) Patent No.: US 9,486,624 B2
(45) Date of Patent: Nov. 8, 2016

(54) DETECTION OF IMPLANTABLE LEAD FAILURES BY DIFFERENTIAL EGM ANALYSIS

(71) Applicant: Lambda Nu Technology LLC, Orono, MN (US)

(72) Inventor: Charles D. Swerdlow, Los Angeles, CA (US)

(73) Assignee: Lambda Nu Technology LLC, Orono, MN (US)

( * ) Notice: Subject to any disclaimer, the term of this patent is extended or adjusted under 35 U.S.C. 154(b) by 58 days.

(21) Appl. No.: 14/224,876

(22) Filed: Mar. 25, 2014

(65) Prior Publication Data

US 2014/0371831 A1    Dec. 18, 2014

Related U.S. Application Data

(60) Provisional application No. 61/834,540, filed on Jun. 13, 2013.

(51) Int. Cl.
*A61N 1/05* (2006.01)
*A61N 1/39* (2006.01)

(52) U.S. Cl.
CPC ........... *A61N 1/0563* (2013.01); *A61N 1/3937* (2013.01)

(58) Field of Classification Search
CPC ............. A61N 1/0563; A61N 1/3937; A61N 2001/083; A61N 1/3622; A61N 1/368
See application file for complete search history.

(56) References Cited

U.S. PATENT DOCUMENTS

| | | |
|---|---|---|
| 3,599,055 A | 8/1971 | Bloom |
| 4,766,549 A | 8/1988 | Schweitzer, III et al. |
| 5,003,975 A | 4/1991 | Hafelfinger et al. |
| 5,231,987 A | 8/1993 | Robson |
| 5,243,980 A | 9/1993 | Mehra |
| 5,361,776 A | 11/1994 | Samuelson et al. |
| 5,405,363 A | 4/1995 | Kroll et al. |

(Continued)

FOREIGN PATENT DOCUMENTS

| | | |
|---|---|---|
| EP | 0288630 B1 | 11/1988 |
| EP | 2032027 B1 | 10/2011 |

OTHER PUBLICATIONS

"Agilent Impedance Measurement Handbook a Guide to Measurement Technology and Techniques 4th Edition," Agilent Technologies, Inc., Jun. 17, 2009, 140 pages.

(Continued)

*Primary Examiner* — Catherine Voorhees
(74) *Attorney, Agent, or Firm* — Patterson Thuente Pedersen, P.A.

(57) ABSTRACT

A method and system for the diagnosis of anomalies in a lead attached to an implantable medical device, such as an implantable cardioverter defibrillator (ICD), including an insulation breach resulting in a short circuit of the high-voltage shock pulse. Determination that the defibrillation pathway is shorted may be made by initial analysis of a Reference EGM and Diagnostic EGM and subsequent analysis of Differential Diagnostic EGMs. Upon determining if a specific defibrillation pathway is shorted, the non-essential defibrillation electrode of that pathway may be excluded from the defibrillation circuit, delivering defibrillation current only between functioning defibrillation electrodes. Alternatively, the ICD system can confirm the presence of a lead anomaly with one or more alternative diagnostic approaches. Patient and remote-monitoring alerts may be initiated.

7 Claims, 10 Drawing Sheets

(56) References Cited

U.S. PATENT DOCUMENTS

| | | | |
|---|---|---|---|
| 5,741,311 | A | 4/1998 | McVenes et al. |
| 5,755,742 | A | 5/1998 | Schuelke et al. |
| 5,897,577 | A | 4/1999 | Cinbis et al. |
| 5,944,746 | A | 8/1999 | Kroll |
| 6,104,954 | A | 8/2000 | Blunsden |
| 6,317,633 | B1 | 11/2001 | Jorgenson et al. |
| 6,445,951 | B1 | 9/2002 | Mouchawar |
| 6,490,486 | B1 | 12/2002 | Bradley |
| 6,928,325 | B2 | 8/2005 | Zhu et al. |
| 7,047,083 | B2 | 5/2006 | Gunderson et al. |
| 7,081,130 | B2 | 7/2006 | Jang |
| 7,120,563 | B2 | 10/2006 | Bechhoefer et al. |
| 7,289,851 | B2 | 10/2007 | Gunderson et al. |
| 7,369,893 | B2 | 5/2008 | Gunderson |
| 7,454,249 | B1 | 11/2008 | Bornzin et al. |
| 7,747,320 | B1 | 6/2010 | Kroll et al. |
| 7,764,998 | B1 | 7/2010 | Raddatz |
| 8,200,330 | B2 | 6/2012 | Kroll et al. |
| 8,352,033 | B2 | 1/2013 | Kroll |
| 8,463,384 | B2 | 6/2013 | Germanson et al. |
| 8,467,872 | B2 | 6/2013 | Hareland |
| 8,498,706 | B2 | 7/2013 | Pei et al. |
| 8,577,457 | B2 | 11/2013 | Miller et al. |
| 8,644,932 | B2 | 2/2014 | Seifert et al. |
| 8,700,156 | B2 | 4/2014 | Kroll |
| 8,812,103 | B2 | 8/2014 | Kroll et al. |
| 8,825,158 | B2 | 9/2014 | Swerdlow |
| 2003/0004552 | A1 | 1/2003 | Plombon et al. |
| 2004/0010303 | A1 | 1/2004 | Bolea et al. |
| 2004/0068301 | A1 | 4/2004 | Waltman et al. |
| 2004/0158290 | A1 | 8/2004 | Girouard et al. |
| 2005/0137636 | A1 | 6/2005 | Gunderson et al. |
| 2005/0187586 | A1 | 8/2005 | David et al. |
| 2005/0256547 | A1 | 11/2005 | Stahmann et al. |
| 2006/0116747 | A1* | 6/2006 | Eick ............... A61N 1/056 607/122 |
| 2006/0135886 | A1 | 6/2006 | Lippert et al. |
| 2006/0241513 | A1 | 10/2006 | Hatlestad |
| 2006/0265038 | A1 | 11/2006 | Hagen et al. |
| 2007/0208387 | A1 | 9/2007 | Mower |
| 2008/0208271 | A1 | 8/2008 | Sih et al. |
| 2008/0309351 | A1 | 12/2008 | Stewart et al. |
| 2009/0099615 | A1 | 4/2009 | Kroll |
| 2009/0270938 | A1* | 10/2009 | Pei ............... A61N 1/056 607/28 |
| 2009/0292331 | A1 | 11/2009 | Gunderson et al. |
| 2009/0306735 | A1 | 12/2009 | Lagercrantz et al. |
| 2010/0179446 | A1 | 7/2010 | Bojovic et al. |
| 2010/0228307 | A1 | 9/2010 | Kroll et al. |
| 2011/0054554 | A1 | 3/2011 | Swerdlow |
| 2011/0054556 | A1 | 3/2011 | Chow |
| 2011/0054558 | A1 | 3/2011 | Gunderson et al. |
| 2011/0160808 | A1 | 6/2011 | Lyden et al. |
| 2011/0160829 | A1 | 6/2011 | Foster et al. |
| 2012/0035491 | A1 | 2/2012 | Mahajan et al. |
| 2012/0191153 | A1 | 7/2012 | Swerdlow et al. |
| 2012/0197331 | A1 | 8/2012 | Germanson et al. |
| 2012/0197365 | A1* | 8/2012 | Germanson ......... A61N 1/0563 607/116 |
| 2013/0013038 | A1 | 1/2013 | Miller |
| 2013/0123871 | A1 | 5/2013 | Kroll |
| 2013/0304139 | A1 | 11/2013 | Musley et al. |
| 2013/0304160 | A1 | 11/2013 | Gunderson et al. |
| 2013/0325079 | A1 | 12/2013 | Kroll et al. |
| 2013/0325080 | A1 | 12/2013 | Kroll et al. |
| 2014/0155947 | A1 | 6/2014 | Kroll et al. |
| 2014/0324123 | A1 | 10/2014 | Kroll et al. |
| 2015/0005862 | A1 | 1/2015 | Kroll et al. |
| 2015/0088213 | A1 | 3/2015 | Swerdlow |
| 2015/0151118 | A1 | 6/2015 | Kroll et al. |
| 2015/0273225 | A1 | 10/2015 | Swerdlow et al. |

OTHER PUBLICATIONS

Armour, Andrew J., et al., "Gross and Microscopic Anatomy of the Human Intrinsic Cardiac Nervous System," Anatomical Record, 1997, pp. 289-298.

Balkhy, Husam H., et al., "Autonomic Ganglionated Plexi: Characterization and Effect of Epicardial Microwave Ablation in a Canine Model of Vagally Induced Actue Atrial Fibrillation," Meeting for the International Society for Minimally Invasive Cardiothoracic Surgery (Abstract), 2006.

Brewer et al., "Low Voltage Shocks Have a Significantly Higher Tilt of the Internal Electric Field Than Do High Voltage Shocks," Angeion Corporation, Jan. 1995, Part II, PACE, vol. 18, pp. 214-220.

Chevalier, P., "Quantitative Study of Nerves of the Human Left Atrium," Heart Rhythm, 2005, pp. 518-522.

Dilling-Boer, Dagmara et al., "Ablation of Focally Induced Atrial Fibrillation: Selective or Extensive?," J. Cardio. Electryphys., 2004, pp. 200-205.

Haissaguerre, Michel et al., "Pulmonary Veins in the Substrate for Atrial Fibrillation: The "venous wave" Hypothesis," 2004, pp. 2290-2292.

Haissaguerre, Michel et al., "Spontaneous Initiation of Atrial Fibrillation by Ecoptic Beats Originating in the Pulmonary Veins," NEJM, 2006, pp. 659-666.

Kilgore, K.L., et al., "Nerve Conduction Block Utilising High-Frequency Alternating Current," Med. Biol. Eng. Comput., 2004, pp. 394-406.

Kumagai, K., et al., "Electrophysiologic Properties of Pulmonary Veins Assessed Using a Multielectrode Basket Catheter," 2004, pp. 2281-2289.

Levy, S., "Characterization of Different Subsets of Atrial Fibrillation in General Practice in France: The ALFA Study," The College of French Cardiologists, Circulation, 1999, pp. 3028-3035.

Lo et al., "Noise-Doman Reflectometry for Locating Wiring Faults," IEEE Transactions on Electromagnetic Compatibility, vol. 47, No. 1, Feb. 2005.

Nathan, H., et al., "The Junction Between the Left Atrium and the Pulmonary Veins: An Anatomic Study of Human Hearts," Circulation, 1966, pp. 412-422.

Oh., S., "Vagal Denervation and Atrial Fibrillation Inducibility: Epicardial Fat Pad Ablation Does Not Have Long-Term Effects," Heart Rhythm, 2006, pp. 701-708.

Oral, Hakan et al., "Pulmonary Vein Isolation for Paroxysmal and Persistent Atrial Fibrillation," Circulation, 2002, pp. 1077-1081.

Pappone, Carlo, "Pulmonary Vein Denervation Enhances Long-Term Benefit After Circumferential Ablation for Paroxysmal Atrial Fibrillation," Circulation, 2004, pp. 327-334.

Patterson, E. et al., "Triggered Firing in Pulmonary Veins Initiated by In Vitro autonomic nerve stimulation," Heart Rhythm, 2005, pp. 624-631.

Patterson, Eugene et al., "Sodium—Calcium Exchange Initiated by the Ca2+ Transient: An Arrhythimia Trigger Within Pulmonary Veins," J. Am. Coll. Cardiol, 2006, pp. 1196-1206.

Po Sunny S., et al., "Rapid and Stable Re-entry within the Pulmonary Vein as a Mechanism Initiating Paroxysmal Atrial Fibrillation," J.Am Coll. Cariol., 2005, pp. 1871-1877.

Po, Sunny S. et al., "Experimental Model for Paroxysmal Atrial Fibrillation Arising at the Pulmonary Vein-Atrial Junctions," Heart Rhythm, 2006, pp. 201-208.

Randall, David C., et al., "Ablation of Posterior Atrial Ganglionated Plexus Potentiates Sympathetic Tachycardia to Behavioral Stress," Comp. Physiol., 1998, pp. 779-787.

Schauerte, P., et al., "Ventricular Rate Control During Atrial Fibrillation by Cardiac Parasympathetic Nerve Stimulation: A Transvenous Approach," J. Am. Coll. Cardiol., 1999, pp. 2043-2050.

Schauerte, Patrick et al., "Catheter Ablation of Cardiac Autonomic Nerves for Prevention of Vagal Atrial Fibrillation," Circulation, 2000, pp. 2774-2780.

Schauerte, Patrick, "Focal Atrial Fibrillation: Experimental Evidence for a Pathophysiologic Role of the Autonomic Nervous System," Cardiovasc. Electrophysiol., 2001, pp. 592-599.

(56) References Cited

OTHER PUBLICATIONS

Scherlag, Benjamin J., et al., "Autonomically Induced Conversion of Pulmonary Vein Focal Firing Into Atrial Fibrillation," J. Am Coll. Cardiol., 2005, pp. 1878-1886.

Scherlag, Benjamin, "Electrical Stimulation to Identify Neural Elements on the Heart: Their Role in Atrial Fibrillation," J. Interv. Card, Electrophysiol, 2005, pp. 37-42.

Tai, C., "Stimulation Analysis of Conduction Block in Unmyelinated Axons Induced by High-Frequency Biphasic Electrical Currents," IEEE T-BME, 2005, p. 1323.

Tchou et al., "The AngeMed Sentinel Implantable Antitachycardia Pacer Cardioverter-Defibrillator," Implantable Cardioverter-Defibrillators: A Comprehensive Textbook, Copyright 1994, pp. 755-761.

Tomasic, "Acute and Chronic High-Frequency Properties of Cardiac Pacing and Defibrillation Leads," Med Biol Eng Comput 50:827-837, 2012.

Ellenbogen, "Performance of ICD Lead Integrity Alert to Assist in the Clinical Diagnosis of ICD Lead Failures: Analysis of Different ICD Leads," Circulation Arrhythmia and Electrophysiology, Oct. 7, 2013.

Swerdlow, "Downloadable Algorithm to Reduce Inappropriate Shocks Caused by Fractures of Implantable Cardioverter-Defibrillator Leads," Circulation Journal of the American Heart Association, Nov. 3, 2008, 9 pages.

Swerdlow, "Downloadable Software Algorithm Reduces Inappropriate Shocks Caused by Implantable Cardioverter-Defibrillator Lead Fractures—A Prospective Study," Circulation Journal of the American Heart Association, Sep. 27, 2010, 8 pages.

PCT Application No. PCT/US2013/043386, filed May 30, 2013, Search Report and Written Opinion dated Sep. 27, 2013, 10 pages.

PCT Application No. PCT/US2013/043389, filed May 30, 2013, Search Report and Written Opinion dated Sep. 5, 2013, 9 pages.

PCT Application No. PCT/US2013/072957, Filed Dec. 4, 2013, Search Report and Written Opinion dated Mar. 6, 2014.

PCT Application No. PCT/US2015/022435, Filed Mar. 25, 2015, Search Report and Written Opinion dated Jun. 29, 2015.

Application and File history for U.S. Appl. No. 12/868,056, filed Aug. 25, 2010, now U.S. Pat. No. 8,825,158. Inventor Swerdlow.

Application and File history for U.S. Appl. No. 13/735,599, filed Jan. 7, 2013, now U.S. Pat. No. 8,700,156. Inventor Kroll.

Application and File history for U.S. Appl. No. 13/842,838, filed Mar. 15, 2013. Inventor Kroll.

Application and File history for U.S. Appl. No. 12/252,310, filed Oct. 15, 2008, now U.S. Pat. No. 8,352,033. Inventor: Kroll.

Application and File history for U.S. Appl. No. 13/843,145, filed Mar. 15, 2013, now U.S. Pat. No. 8,812,103. Inventors: Kroll et al.

Application and File history for U.S. Appl. No. 13/833,477, filed Mar. 15, 2013. Inventors: Kroll et al.

Application and File history for U.S. Appl. No. 14/224,281, filed Mar. 25, 2014. Inventors: Kroll et al.

Application and File history for U.S. Appl. No. 14/203,688, filed Mar. 11, 2014. Inventors: Kroll et al.

Application and File history for U.S. Appl. No. 14/224,335, filed Mar. 25, 2014. Inventors: Kroll et al.

Application and File history for U.S. Appl. No. 14/453,679, filed Aug. 7, 2014. Inventors: Kroll et al.

Application and File history for U.S. Appl. No. 14/472,027, filed Aug. 28, 2014. Inventors: Kroll et al.

\* cited by examiner

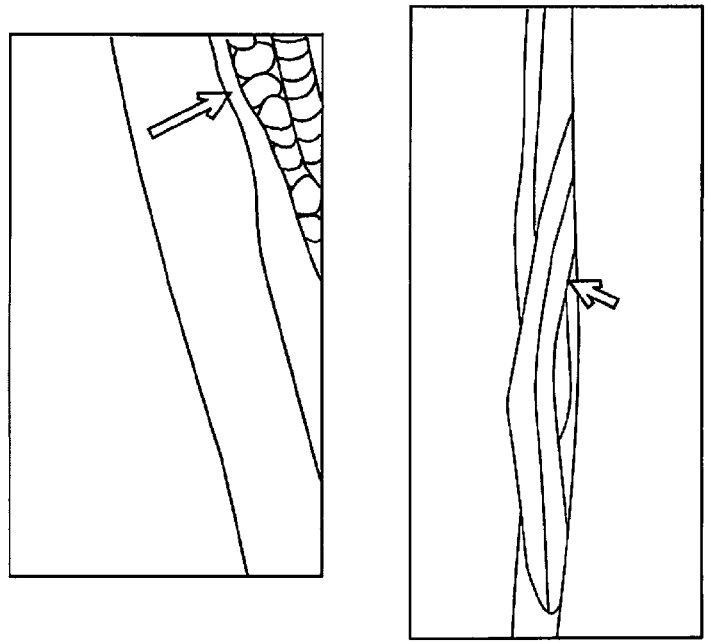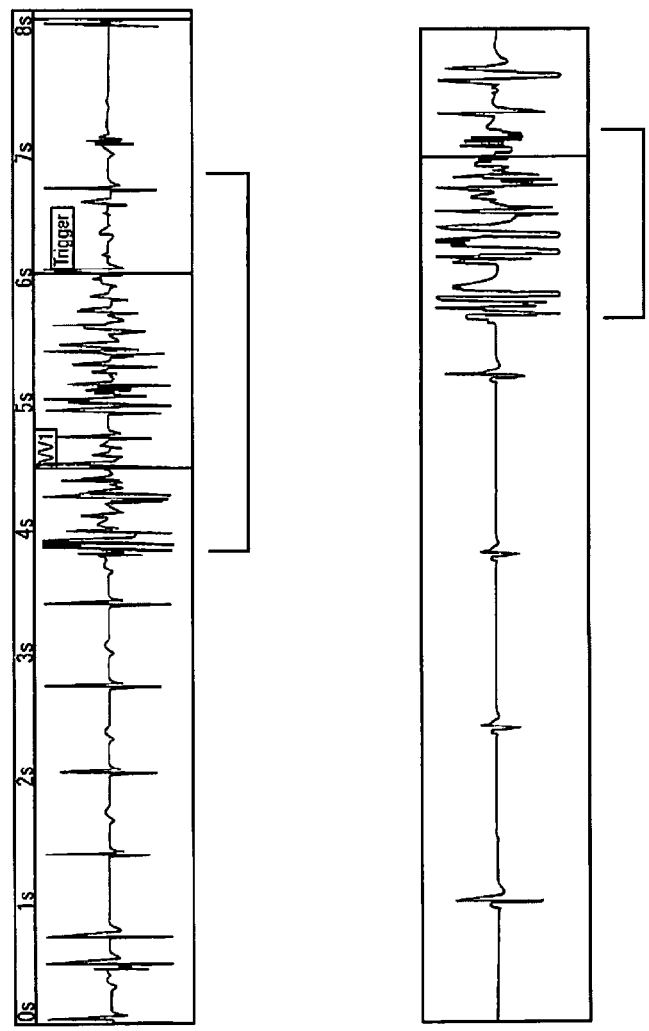
Fig. 4

Fig. 5

| Lead Sensing Configuration / Lead Shock Configuration | True-Bipolar | Integrated-Bipolar |
|---|---|---|
| Dual-Coil | | |
| Reference EGM | Tip-Ring | Tip-CAN |
| Diagnostic EGM | Coil-Coil | Coil-Coil |
| Single-Coil | | |
| Reference EGM | Tip-Ring | Tip-CAN |
| Diagnostic EGM | Tip RV-Coil | Tip-RV Coil |

| | Purpose | Determinant | True-Bipolar | Integrated-Bipolar |
|---|---|---|---|---|
| Reference EGM | Sense true ventricular events | Lead Sensing configuration | Tip-Ring | Tip-CAN |
| | | | Single Coil | Dual Coil |
| Diagnostic EGM | Record anomalies from shock coils | Shock electrode configuration | Tip-RV Coil | Coil-Coil |

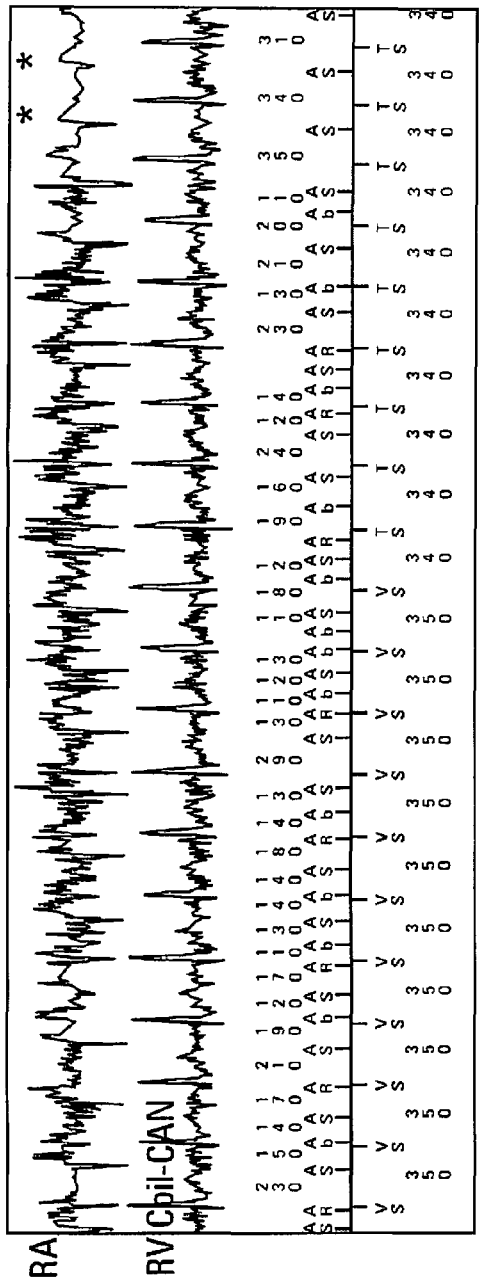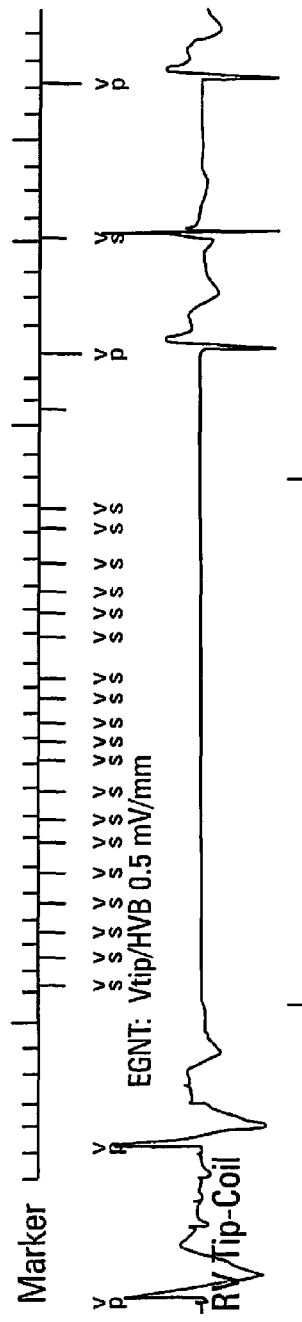

DETECTION OF IMPLANTABLE LEAD FAILURES BY DIFFERENTIAL EGM ANALYSIS

RELATED APPLICATION

The present application claims the benefit of U.S. Provisional Application No. 61/834,540, filed Jun. 13, 2013, which is incorporated herein in its entirety by reference.

FIELD OF THE INVENTION

The present invention relates, generally, to scientific and medical methods for diagnosis of conductor anomalies. More particularly, the invention relates to methods and apparatus for diagnosis of conductor anomalies, such as insulation breaches resulting in the shorting of a defibrillation pathway or circuit, in an implantable lead for an implantable medical device, such as an implantable cardioverter defibrillator (ICD). In various embodiments, detection of an implantable lead failure utilizes electrogram (EGM) analysis, in particular, analysis of recordings of differential high-voltage EGMs to identify the source of noncardiac signals.

BACKGROUND

The long-term reliability and safety of implantable cardiac leads is critical to the function of implanted medical devices. Conversely, lead anomalies constitute a major cause of morbidity. Representative examples of such medical devices include, but are not limited to, pacemakers, vagal nerve stimulators, pain stimulators, neurostimulators, and implantable cardioverter defibrillators (ICDs). For example, early diagnosis of ICD lead anomalies is important to reduce morbidity and/or mortality from loss of pacing, inappropriate ICD shocks, and/or ineffective shock or pacing treatment of ventricular tachycardia or ventricular fibrillation. Early diagnosis of anomalies in implantable cardiac leads is critical to improving reliability of ICD therapies.

Multilumen ICD defibrillation electrodes or leads include one or more high-voltage conductors and one or more pace-sense conductors. The leads can be implanted as subcutaneous, epicardial, or intravascular leads. Clinically, the most important lead failures have occurred in transvenous right ventricular (RV) defibrillation leads. These leads comprise a distal tip electrode with a fixation mechanism that anchors the lead to the RV myocardium, proximal terminals that connect to the generator, and a lead body connecting the two. The "multilumen" lead body consists of a flexible, insulating cylinder with three to six parallel, longitudinal lumens through which conductors run from the proximal terminals to small pace-sense electrodes and larger shock coil electrodes. RV defibrillation leads have a distal shock coil in the RV. The vast majority of presently implanted transvenous ICD systems deliver therapeutic shocks between the RV shock coil with one polarity during the shock and the housing ("CAN") of the generator ("active" or "hot" CAN), which has opposite polarity. Defibrillation leads may have either one or two shock coils and one or two dedicated sensing electrodes.

Dual coil vs. single coil leads: Dual-coil leads have an additional proximal shock coil, which usually lies in the superior vena cava (SVC). Dual-coil leads usually deliver shocks with the SVC shock coil electrically linked to the CAN and opposite in polarity to the RV shock coil. Alternatively, shocks may be delivered solely between the RV and SVC shock coils, without using the CAN as a shock electrode.

Integrated vs. true bipolar lead sensing configurations: Integrated-bipolar leads have a single sensing electrode on the tip. They sense the "integrated-bipolar" signal between the tip electrode and RV coil. True bipolar leads have an additional sensing-ring electrode. Their sensing configuration can either be "true bipolar" between the tip electrode and a ring electrode or "integrated-bipolar."

Insulation breaches have been known to result in a functional failure of conductors within the lead or interactions among said conductors. Functional failure of a pace-sense conductor may result in symptoms caused by loss of pacing functions for bradycardia, cardiac resynchronization, or antitachycardia pacing. Functional failure of a high-voltage conductor may result in fatal failure of cardioversion or defibrillation. In addition, conductor interactions involving pace-sense conductors may result in oversensing leading to inappropriate shocks or failure to pace. Interactions involving high-voltage electrodes may result in shorting the shock output, preventing life saving therapy from reaching the patient and potentially damaging the pulse generator irrevocably.

Thus, one major goal is high sensitivity of diagnosis for the identification of lead failures at the subclinical stage, before they present as a clinical problem. A second major goal is high specificity because a false positive provisional clinical diagnosis of lead failure may trigger patient anxiety and lead to potentially avoidable diagnostic testing. A false positive clinical diagnosis of lead failure may result in unnecessary lead replacement, with corresponding expense and surgical risk.

Insulation breaches or conductor fractures occur most commonly at two regions along the course of a defibrillation lead. The first region is within the pocket, caused either by abrasion of the lead insulation by pressure from the housing ("CAN") of the pulse generator (lead-CAN abrasion) or twisting and rubbing of the lead within the pocket against other elements of the same or a different lead (lead-lead abrasion). The second region is the intracardiac region between or under the shock coils in a dual-coil lead or proximal to the shock coil in a single coil lead. The second region is a common site of insulation breach for leads in the St. Jude Riata® family, for example, which is subject to "inside-out" insulation breach due to motion of the internal cables relative to the outer insulation. Multiple potential interactions are possible, including, inside-out abrasion of the cable to the RV shock coil against the proximal (SVC) shock coil, resulting in a short circuit within the lead. The lead may also be damaged between the clavicle and first rib, where the lead is subject to "clavicular crush," usually resulting in conductor fracture.

What is needed is a method and apparatus that focuses on detection of in-pocket lead problems but where the ideas can be extended to problems in other locations along the lead.

Insulation breaches of ICD defibrillation leads within the pocket can result in abrasion of the insulation around any of the cable conductors including the conductor to the RV coil, RV sensing ring, or SVC coil. One of the most dangerous conditions is abrasion of the insulation around the conductor of the RV coil (coil-CAN abrasion). This abrasion results in a short circuit between the CAN electrode and the right ventricular (RV) coil, which prevents defibrillation current from reaching the heart in the event of life threatening ventricular tachycardia or ventricular fibrillation. If the shock is delivered, extremely high current flowing through the shorted output circuit of the ICD may irrevocably damage the generator's components. (Hauser R G, McGriff D, Retel L K. Riata implantable cardioverter-defibrillator lead failure: analysis of explanted leads with a unique insulation defect. Heart Rhythm. 2012; 9:742-749; Hauser R G, Abdelhadi R H, McGriff D M, Kallinen Retel L. Failure of a novel silicone-polyurethane copolymer (Optim) to prevent implantable cardioverter-defibrillator lead insulation abrasions. Europace. 2013; 15:278-283.)

Many ICDs contain circuits that protect the electrical integrity of the generator against shorted high voltage outputs. These circuits abort the shock if the current in the output circuit is sufficiently high, indicative of a short circuit diverting current from the heart. Although such protective circuitry may prevent damage to the generator, the potentially lifesaving shock does not reach the patient. U.S. Pat. No. 7,747,320 to Kroll teaches a backup defibrillation mode method which excludes shorted electrodes during a shock. However, this method applies only during shock delivery of a high output shock in response to detection of ventricular fibrillation or tachycardia by the ICD. Further, such a high-output shock still may have enough energy to ablate additional insulation which will exacerbate the insulation breach and potentially even "spot weld" the exposed conductor to the housing, exacerbating the short circuit. Further, this method cannot be used with single coil leads and it result in shock delivery through only part of the intended defibrillation pathway, with unknown defibrillation efficacy.

Existing technology for diagnosis of lead anomalies in an ICD lead is believed to have significant limitations and shortcomings, especially with regard to diagnosis of high-voltage insulation breaches prior to shock delivery. ICDs routinely deliver low voltage pulses, on the order of about 1.0 volts to about 15.0 volts, or switched AC pulse trains to measure the impedance of the high voltage shock pathway. However, these low-voltage measurements of shock-electrode impedance may not identify insulation breaches in which the insulation's dielectric properties remain intact at low voltages but break down during high-voltage shocks. Clinical case reports indicate that high-voltage insulation breaches may not be detected by these low voltage measurements, and, despite nominal values of such measurements, high voltage clinical shocks have short circuited, preventing the current from reaching the heart and defibrillating ventricular fibrillation. (Shah P, Singh G, Chandra S, Schuger C D. Failure to deliver therapy by a Riata lead with internal wire externalization and normal electrical parameters during routine interrogation. J Cardiovasc Electrophysiol. 2013; 24:94-96.)

U.S. patent application Ser. No. 13/843,145 of Swerdlow and Kroll, filed Mar. 15, 2013 seeks to overcome the limitations of low-voltage pulses for measuring shock impedance by delivering high-voltage, extremely-short ("sliver") test pulses. However, it may not be practical to deliver such pulses on a routine, daily basis because of the battery power required. Further, if these pulses cause patient discomfort, their delivery may be restricted.

Existing technology for diagnosis of anomalies in pacemaker leads and low voltage lead components is also believed to have significant limitations and shortcomings, especially with regard to early diagnosis. The primary method in the prior art for monitoring pacemaker lead integrity is periodic measurement of electrical resistance, commonly referred to as "impedance monitoring." Impedance monitoring uses single pulses. Various methods are well-known in the art. These methods provide a value of impedance close to the direct-current resistance.

In the circuit being measured, most of the resistance is at the electrode-tissue interface of the high-resistance tip electrode, and variations of up to 10% in this value are common. Each individual pace-sense conductor (for example, the conductor to the tip electrode or the ring electrode) contributes less than 10% to the measured resistance. Thus even if the resistance in a single conductor doubled or tripled, the overall measured resistance will remain within the expected range. Measurements indicate that resistance does not exceed the expected range until the conductor has lost most of its structural integrity. Thus, resistance measurements are insensitive to partial loss of conductor integrity. Further, resistance measurements have limited specificity. A single, out-of-range value may be an artifact, and marked increases can occur at the electrode-myocardial interface.

Hafelinger et al. (U.S. Pat. No. 5,003,975) and Cinbis et al. (U.S. Pat. No. 5,897,577) summarize some of these methods, which include measurements made directly using either a single pacing pulse or a single independent pulse used only for measuring resistance. McVenes et al. (U.S. Pat. No. 5,741,311) describe use of a longer burst of alternating current at a single frequency. The purpose of these longer (about 100 ms) pulses is to drive the system to a steady-state condition that is not achieved by single, short (less than 1 ms) pacing pulses. Schuelke et al. (U.S. Pat. No. 5,755,742) describe a method for measuring resistance of defibrillation electrodes by applying a test voltage applied to a different excitation current pathway. Kroll et al. (U.S. Pat. No. 5,944,746) described an automated method for periodic measurement of the resistance of the high-voltage (defibrillating) coil in ICD electrodes. Gunderson et al. (U.S. Pat. No. 7,047,083) described a method and system for automated, periodic, measurements of resistance in conductors attached to an ICD or pacemaker. However, these methods identify lead anomalies before inappropriate shocks in only about a third of ICD patients who have conductor fractures and an even lower fraction with insulation breaches. (Swerdlow C D, Gunderson B D, Ousdigian K T, Abeyratne A, Sachanandani H, Ellenbogen K A. Downloadable software algorithm reduces inappropriate shocks caused by implantable cardioverter-defibrillator lead fractures: a prospective study. *Circulation*. 2010; 122:1449-1455) (Sung R K, Massie B M, Varosy P D, Moore H, Rumsfeld J, Lee B K, Keung E. Long-term electrical survival analysis of Riata and Riata ST silicone leads: National Veterans Affairs experience. Heart Rhythm. 2012; 9:1954-1961) (Ellenbogen K A, Gunderson B D, Stromberg K D, Swerdlow C D. Performance of Lead Integrity Alert to assist in the clinical diagnosis of implantable cardioverter defibrillator lead failures: analysis of different implantable cardioverter defibrillator leads. Circ Arrhythm Electrophysiol. 2013; 6:1169-1177.)

A different method for monitoring defibrillation lead sensing integrity is based on sensing of rapid nonphysiological signals associated with lead conductor fractures by the ICD pulse generator. Repetitive oversensing of nonphysiologically-short intervals may indicate lead conductor fracture even if lead resistance is normal. Gunderson et al. (U.S. Pat. No. 7,289,851) described a Lead-Integrity Alert that incorporates both ICD-based measures of oversensing based on the nonphysiologically-rapid rate of sensed signals and periodic measurements of resistance. This method, combined with automatic ICD reprogramming, improves warning time before inappropriate shocks caused by lead-related oversensing. Nevertheless, approximately 40% of patients receive inappropriate shocks with conductor fracture (Swerdlow C D, Gunderson B D, Ousdigian K T, Abeyratne A, Sachanandani H, Ellenbogen K A. Downloadable software algorithm reduces inappropriate shocks caused by implantable cardioverter-defibrillator lead fractures: a prospective study. *Circulation*. 2010; 122:1449-1455).

In addition to limited sensitivity, present methods for diagnosing lead anomalies have limited specificity resulting in false positive diagnostics (Ellenbogen K A, Gunderson B D, Stromberg K D, Swerdlow C D. Performance of Lead Integrity Alert to assist in the clinical diagnosis of implantable cardioverter defibrillator lead failures: analysis of different implantable cardioverter defibrillator leads. Circ Arrhythm Electrophysiol. 2013; 6:1169-1177).

Evaluation of false positive diagnostics adds cost and work to medical care and may contribute to patient anxiety. If a false-positive diagnostic is not diagnosed correctly, patients may be subject to unnecessary surgical lead replacement with its corresponding risks, and clinical reports document that this has happened (Swerdlow C D, Sachanandani H, Gunderson B D, Ousdigian K T, Hjelle M, Ellenbogen K A. Preventing overdiagnosis of implantable cardioverter-defibrillator lead fractures using device diagnostics. J Am Coll Cardiol. 2011; 57:2330-2339).

Gunderson et al. (U.S. Pat. No. 7,369,893) further describes a method for withholding delivery of ICD shocks if ventricular fibrillation is detected from analysis of the pace-sense lead, but not confirmed by analysis of the high-voltage lead. The presumption is that these signals do not represent true cardiac activations. However, this method requires sufficient oversensing of spontaneously-generated, unpredictable, rapid noncardiac signals to cause inappropriate detection of ventricular fibrillation clinically. Thus, it does not provide early diagnosis of conductor anomalies. Further, withholding shocks for ventricular fibrillation detected on the near-field electrogram has an inherent risk of withholding life-saving therapy, however small, if a false positive test outcome occurs. It is thus not the preferred approach to diagnosis conductor fracture. St. Jude Medical has also introduced an algorithm ("SecureSense®") that incorporates features similar to those described in U.S. Pat. No. 7,369,893.

Gunderson (U.S. Patent Publication No. 2011/0054558) also disclosed applying a pacing stimulus through a pace-sense channel and monitoring the same sensing channel for the occurrence of rapid, anomalous signals immediately after the pacing pulse. This method has the potential to detect anomalous signals when they are not occurring spontaneously, but it has several limitations. First, only conductor fractures are known to exhibit this behavior of pacing-induced lead "noise." Insulation breaches have not been reported to cause pacing-induced lead noise. Thus, this method does not apply to them. Second, pacing induced lead noise is inconsistent. It does not happen every time a pacing pulse or train is delivered. The infrequency with which pacing-induced lead noise is identified clinically and the infrequency of reports in the medical literature suggests it is uncommon. Thus this method is likely to be insensitive. Third, it does not apply to failures of high-voltage cables or coils.

Each of these algorithms identifies lead failures using abnormal signals on the sensing channel. Thus, they cannot identify failures of high-voltage components including the shock coils and their cables, and they cannot discriminate such signals from other rapid, oversensed signals. What is desired is a method to provide sensitive and specific diagnosis of lead anomalies at the subclinical stage, a method that applies to both pace-sense and shock components.

SUMMARY OF THE INVENTION

The disclosed embodiments relate to the diagnosis of conductor anomalies, such as an insulation breach resulting in a short circuit, in an implantable lead of an implantable medical device, such as an implantable cardioverter defibrillator (ICD). In various embodiments, detection of an implantable lead failure utilizes electrogram (EGM) analysis, in particular, analysis of differential recordings of EGMs recorded from various combinations of ICD electrodes to detect anomalous signals that indicate lead failure. In various embodiments, this may result in sending alerts or excluding shock electrodes from the defibrillation pathway based on EGMs that record signals from noncardiac sources, indicating the presence of a lead anomaly. Some of the advantages over previously-described methods are that various embodiments can be implemented without delivering a shock, and/or can identify a lead anomaly despite impedance measurements within the nominal range.

In various embodiments, two underlying concepts are relied upon to analyze and identify implantable cardiac lead anomalies at the subclinical stage, before these potential anomalies present as a clinical problem, and do so with a high sensitivity and specificity. First, noncardiac signals indicating a lead anomaly can be identified on a Diagnostic EGM that is likely to record signals indicative of lead anomalies by a combination of processing the Diagnostic EGM and comparing it to a Reference EGM that is unlikely to record the same signals indicative of lead anomalies. Second, differential EGM recording can be used to determine which high-voltage conductor(s) or shock coil(s) are the source of abnormal signals caused by the lead anomaly so that the ICD system may intervene to prevent delivering a shock into a shorted high-output circuit.

The use of EGM analysis to identify anomalies related to high-voltage components also must overcome at least three problems that do not apply to existing methods used to detect pace-sense conductor fractures. First, pace-sense EGMs are monitored continuously in all ICDs, but shock electrode EGMs are not. Second, the vast majority of noncardiac signals associated with pace-sense conductor fractures are thought to be caused by potentials that originate at the fracture site and have relatively typical EGM characteristics, often described as "noise." In contrast, there are multiple, very different sources of EGMs associated with insulation failures, and their signal characteristics vary. For example, the source of noncardiac signals due to insulation failure within the lead body is thought to be direct metal-on-metal contact between conductors within the lead. However, noncardiac signals that indicate insulation breaches in the surgical "pocket" originate in the pectoral muscle (pectoral myopotentials). Third, small, closely-spaced, true-bipolar electrodes have a limited field of view; when leads are intact, they rarely record signals other than true right ventricular EGMs. In contrast, EGMs recorded between large, widely-spaced shock electrodes have a larger field of view and, even in intact leads, often record both cardiac atrial signals and noncardiac signals. For example, integrated-bipolar electrodes may record diaphragmatic myopotentials. As another example, shock EGMs that include the CAN commonly record pectoral myopotentials because the CAN electrode has a large conductor surface in close proximity to the large pectoral muscle. Thus pectoral myopotentials may represent the source of anomalous signals in leads with in-pocket insulation breaches, but they may also be recorded from electrically-intact shock electrodes. Embodiments for identifying insulation breaches must be able to distinguish among these cases.

A basic method of detecting a short in an ICD capable of recording simultaneous EGMs in accordance with various embodiments of the present invention utilizes a Reference EGM and Diagnostic EGM, each of which are monitored continuously. The purpose of the Diagnostic EGM is to be sensitive to anomalous noncardiac electrical signals that are indicative of a lead anomaly that are recorded from conductors attached to one or more "high-voltage" shock coils. (Note, such EGMs are referred to as "high-voltage" or "shock" EGMs because they are recorded from at least one high-voltage conductor to a shock coil; this term does not indicate that the Diagnostic EGM signals themselves have high voltage amplitudes or that they are recorded during a shock.) The Diagnostic EGM is determined by the number of shock coils on the lead.

The purpose of the Reference EGM is to sense true ventricular electrical activations, but not signals indicative of lead anomalies indicating an electrical abnormality relating to a high-voltage lead component. The Reference EGM is determined by the configuration of the lead's sensing electrodes. In certain embodiments, the choice of the Diagnostic EGM is based on number of shock coils and the choice of the Reference EGM is based on sensing configuration.

While the embodiments disclosed herein may apply to both high-voltage fractures and insulation breaches, the embodiments will be discussed in relation to insulation breaches in which failure of insulation between shock electrodes of opposite polarity could result in shorted output of high-voltage shocks. In various embodiments, if a specific defibrillation pathway is determined to be shorted, the non-essential electrode associated with the shorted pathway is excluded from the defibrillation circuit, delivering defibrillation current only between functioning defibrillation electrodes. In addition to excluding the non-essential electrode, the response can include a patient alert, and the lead anomaly can be confirmed using other diagnostic techniques.

The above summary of the various embodiments of the invention is not intended to describe each illustrated embodiment or every implementation of the invention. This summary represents a simplified overview of certain aspects of the invention to facilitate a basic understanding of the invention.

BRIEF DESCRIPTION OF THE DRAWINGS

The invention may be more completely understood in consideration of the following detailed description of various embodiments of the invention in connection with the accompanying drawings, in which:

FIG. 4 illustrates noncardiac signals recorded from in-pocket insulation breaches.

FIG. 5 is a table indicating various embodiments with different combinations of Reference and Diagnostic EGMs for commonly-used ICD lead configurations.

FIGS. 8a and 8b display representative intracardiac EGMs.

Figure 1:
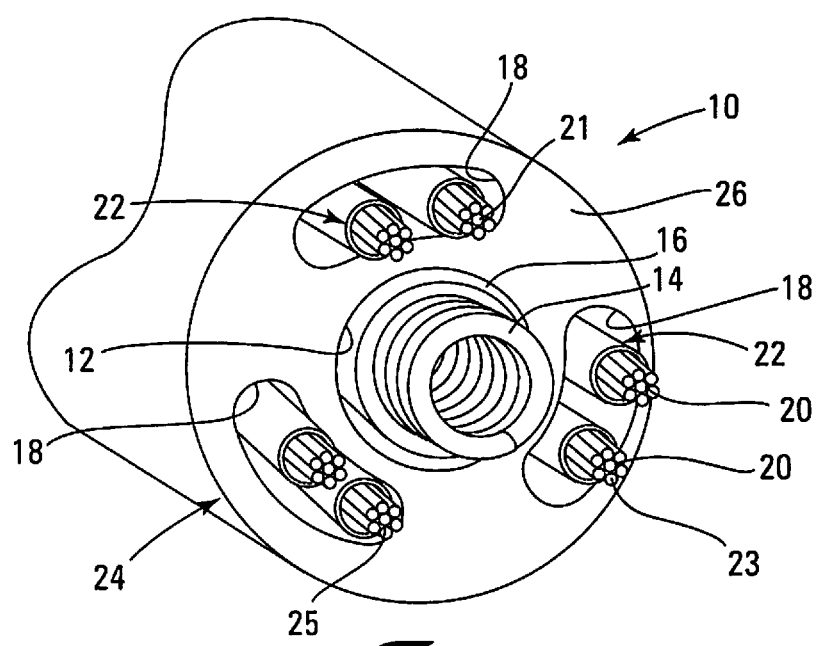
FIG. 1 depicts examples of a multilumen ICD lead.

While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the invention as defined by the appended claims.

DETAILED DESCRIPTION

Disclosed is a method for diagnosis of anomalies in leads attached to implantable medical devices, such as an implantable cardioverter defibrillator (ICD). In ICD systems this method applies to detecting insulation breaches resulting in the shorting of a defibrillation pathway as well as to other anomalies such as such as fractures of high-voltage conductors. It will be discussed in relation to insulation breaches in which failure of insulation between shock electrodes of opposite polarity result in shorted high output.

As disclosed herein, the RV coil is considered to be the anode (positive) and the SVC coil and CAN are considered to be the cathodes (for the primary or first phase of the defibrillation shock). However, the polarity can be reversed.

FIG. 1 illustrates one example of an implantable cardiac lead 10. The lead 10 is comprised of a lumen 12 and center inner pacing coil 14 surrounded by polytetrafluoroetheylene (PTFE) insulation 16, a plurality of lumens 18 each containing at least one conductor 20 with each conductor 20 surrounded by ethyltetrafluoroetheylene (ETFE) insulation 22, the primary silicone elastomer insulation of the lead body 26 and an optional outer insulating layer 24 usually comprised of polyurethane or a copolymer of silicone and polyurethane. The conductors 20 include a sense conductor 21, a high voltage RV conductor 23 and a high voltage SVC conductor 25. The plurality of lumens 18 is disposed in the silicone insulation 26. The conductors 20 carry electric current to the pace-sense electrodes 66, 68, high voltage RV coil 64 and high voltage SVC coil 62 (FIG. 2).

Figure 2:
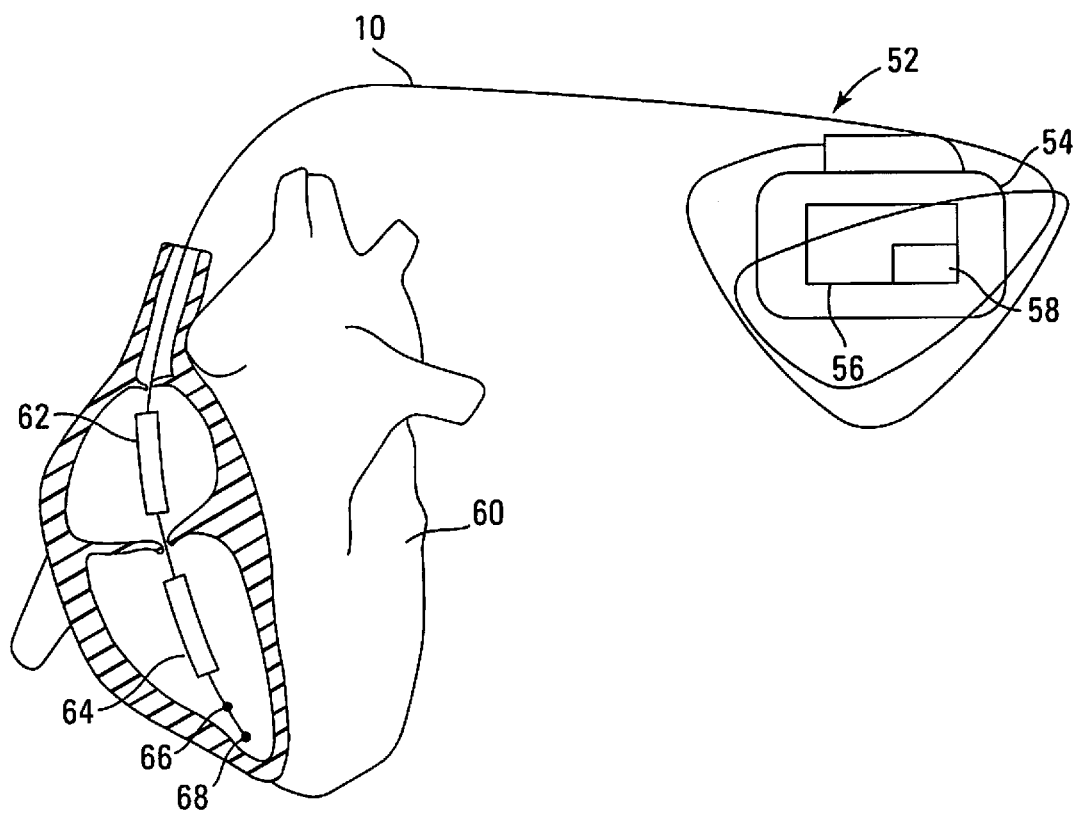
FIG. 2 illustrates an ICD pulse generator connected to a patient's heart via a transvenous cardiac lead used for pacing and defibrillation and further illustrates a short from the RV conductor to the ICD housing, in which the disclosed embodiments may be practiced.

FIG. 2 depicts an ICD system implanted in the chest of a patient having an outer housing 54, commonly referred to as a "CAN," inner circuitry 56 and a battery 58. Connection is made to the heart 60 via the lead 10. The lead 10 is often wrapped around the CAN 54 in the pocket until it exits, shown as reference number 52, the pocket on its intravascular course. The lead 10 can have an optional proximal defibrillation coil 62, which is commonly referred to as the SVC Coil 62. The lead 10 also has a distal defibrillation coil 64 or RV Coil 64. Also shown is the optional "ring" pacing-sensing electrode 66. Located at the distal end of the lead 10 is the "tip" pacing-sensing electrode 68.

Figure 3:
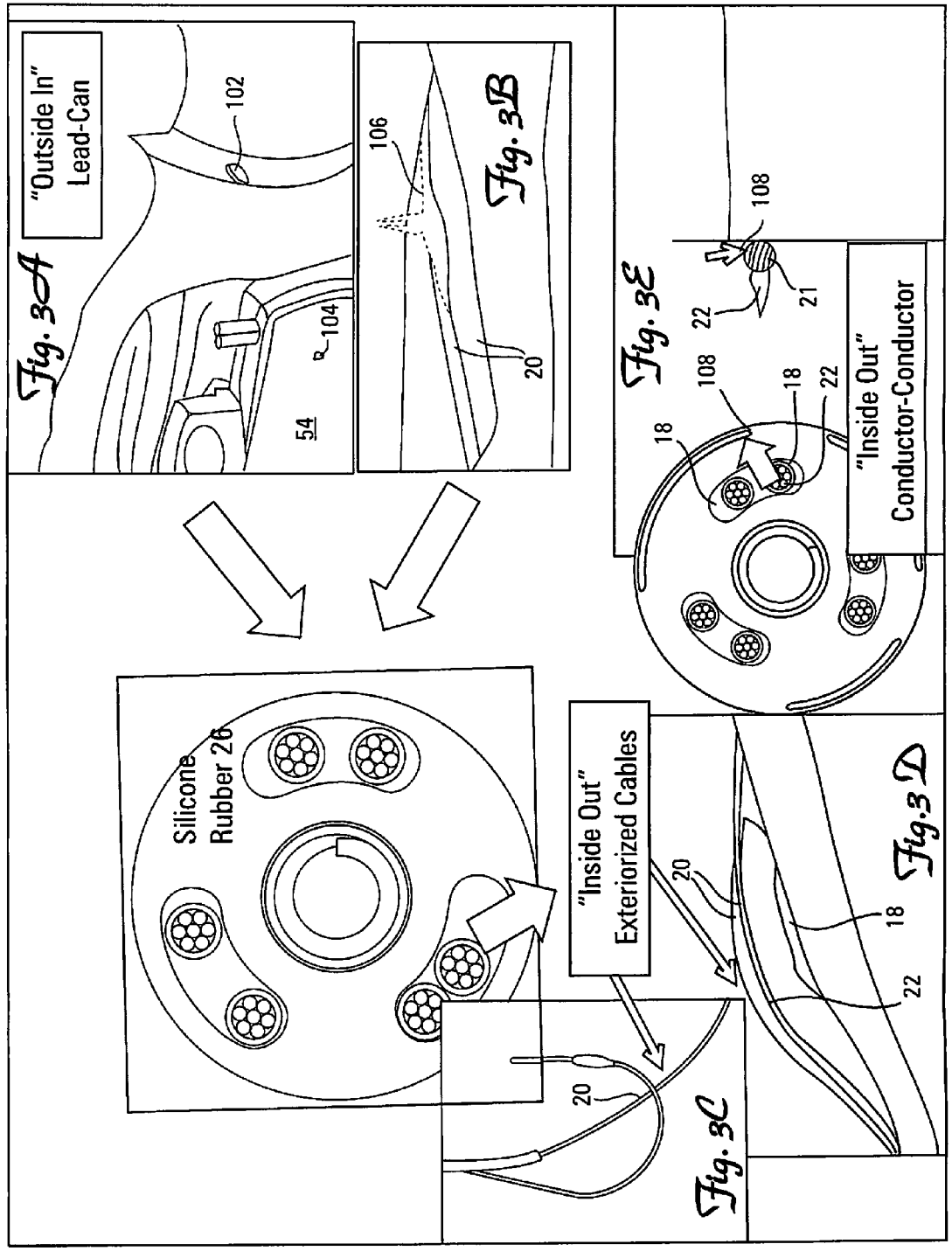
FIGS. 3a through 3e illustrate the various types of abrasions that may result in insulation breaches.

FIG. 3a illustrates two primary types of abrasions that may result in silicone insulation breaches of the multilumen defibrillation lead 10. FIG. 3a shows an in-pocket abrasion at the CAN 54 showing a defect 102 in the lead 10 body's insulation 24 and a corresponding char mark 104 on the CAN 54 after a short circuit during shock resulted in extremely high current flow. FIG. 3b shows another in-pocket abrasion 106, exposing the dual conductors 20 to the RV Coil 64. FIGS. 3c and 3d show radiograph and photograph, respectively, of inside-out abrasion of cables 20 through the walls of their lumen 18 with intact ETFE inner insulation 22. FIG. 3e shows abrasion of pace-sense cable 21 through the wall of its lumen 18 against RV Coil 64 further abrading the ETFE inner insulation 22 to permit direct metal-to-metal contact shorting 108 the cable 20 to the coil 64.

FIG. 4 shows photographs of two in-pocket abrasions involving both outer silicone insulation 24 and corresponding inner ETFE insulation 22 (arrows) along with corresponding noncardiac signals with amplitude comparable to the true ventricular EGMs (brackets).

Embodiments are described that perform testing to determine if a specific defibrillation pathway or conductor 20 forms a short circuit with the CAN 54 or another pathway or conductor 20. If such a short is present, the potential responses may include removal of the shorted non-essential defibrillation electrode from the shock circuit so that defibrillation current is delivered only between functioning defibrillation electrodes, transmitting an alert, confirming the finding with differential sliver pulse, or a combination thereof. Consider a pectoral, transvenous ICD with a dual-coil defibrillation lead. In the event of, for example, a short in the RV Coil-CAN defibrillation pathway, caused by, for example, an in-pocket, lead-CAN abrasion, the CAN 54 can be excluded from the defibrillation circuit, so that defibrillation current is delivered only between the RV defibrillation coil 64 and SVC defibrillation coil 62. Alternatively, if there is a short involving the SVC Coil 62 or its conductor 20, the SVC Coil 62 can be excluded from the defibrillation circuit, so that defibrillation current is delivered only between the RV Coil 64 and CAN 54.

As noted previously, a basic method of detecting a short utilizes continuous monitoring of both a Diagnostic EGM sensitive to signals from lead anomalies and a Reference EGM that records true ventricular electrical activations, but is insensitive to signals from lead anomalies involving high-voltage components. FIG. 5 is a table indicating the specific pairs of Reference and Diagnostic EGMs for each the various electrode configurations presently used in RV defibrillation leads.

In one embodiment, the Diagnostic EGM is determined by the number of shock coils on the lead. For dual-coil leads, it is the Coil-Coil EGM recorded between the RV Coil and SVC Coil. This EGM is selected to ensure recording of an anomaly involving either shock coil and avoid recording pectoral myopotentials, which are often present on the more commonly recorded shock EGMs that include the CAN 54. For single-coil leads, it is the integrated-bipolar (Tip-RV Coil) EGM. This EGM may record diaphragmatic myopotentials, and—as discussed below—the method includes a step that makes it insensitive to diaphragmatic myopotentials.

In one embodiment, the Reference EGM is determined by the configuration of the lead's sensing electrodes. In a true-bipolar leads, the obvious choice is the Sensing (Tip-Ring) EGM, which has a small field of view and is insensitive to anomalies of the high-voltage components. In integrated-bipolar leads, the Tip-CAN (unipolar) EGM serves as the Reference EGM. Most ICDs do not permit recording this EGM, and it has not previously served a functional role.

However, for integrated-bipolar leads, this EGM is the only option that does not include a high-voltage electrode. This EGM may record pectoral myopotentials. However, because it is used as a Reference EGM rather than a Diagnostic EGM, it will be seen that these myopotentials do not result in false positive determination of a lead anomaly.

Figure 6:
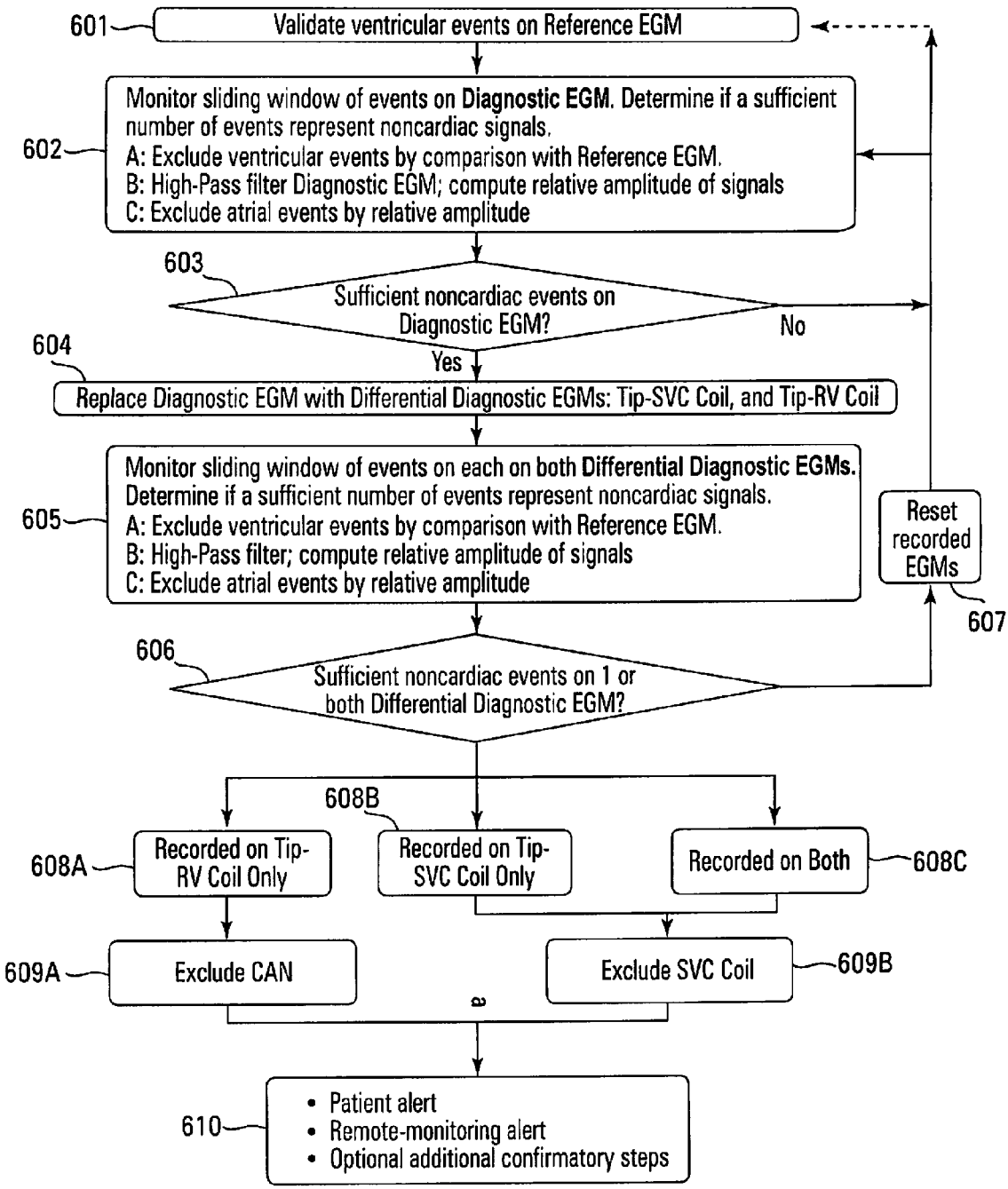
FIG. 6 is a flowchart depicting one embodiment of detecting a short using differential EGM recording for a dual-coil lead.

FIG. 6 is a flowchart depicting one embodiment of detecting a short using differential EGM recording for a dual-coil lead in accordance with the present disclosure. Optionally, ventricular events are validated on the Reference EGM 601. This can be especially important for the Tip-CAN Reference EGM used on integrated-bipolar leads to exclude pectoral myopotentials. The underlying concept is that pectoral myopotentials, routinely recorded on EGMs that include the CAN 54, have low amplitude if the lead's insulation is intact (FIG. 8a). True ventricular EGMs are confirmed (validated) by one of several methods known in the art, such as comparison with a template or excluding rapid EGMs separated by extremely short intervals. As a representative example, signals are analyzed only if the two preceding ventricular intervals each exceed a value well within the physiological range, such as 400 ms. Then, the amplitude of these events on the Reference EGM are calculated by one of several methods known in the art, such as the median amplitude, either in a specific time window updated periodically (e.g. daily, hourly) or on a real time basis (e.g. validated EGMs in the same time window analyzed for the presence of lead anomaly). In addition to such unequivocal ventricular events on the Reference EGM, events are considered to probably represent ventricular activation (probable ventricular events) if they could reasonably represent premature beats, by fulfilling both an amplitude and interval criterion. They must exceed a percentage of the amplitude of unequivocal ventricular events (e.g., 50%) and the preceding two ventricular intervals must not be shorter than physiological intervals of typical premature beats (e.g., 250 ms). For the purpose of comparison with the Diagnostic EGM, a ventricular event is confirmed and considered present on the Reference EGM if it is either unequivocal or probable. Additionally, the Diagnostic channel may be optimized by adjusting the amplifier gain so that the maximum amplitude of the unequivocal ventricular events is between 50 and 75% of the dynamic range of the amplifier.

Unlike prior art techniques that focus on sensed events from the Sensing EGM, this embodiment determines if a sufficient number of sensed events on the Diagnostic EGM represent noncardiac signals by comparing them with ventricular events on the Reference EGM 602. Specifically, substeps determine that they do not represent ventricular activations 602A or atrial activations 602B, 602C. Events on Diagnostic EGM are determined to represent ventricular activations if they occur within a time window centered on the ventricular event as determined by the Reference EGM. For purposes of illustration, this window has a total duration of 200 ms. In 602B, the Coil-Coil Diagnostic EGM is high-pass filtered by one of several methods known in the art, such as analog or digital filtering (either finite or infinite impulse response). In 602C, atrial events are identified on the Diagnostic EGM so that they are not considered noncardiac signals. This step may utilize the fact that the dominant frequency of atrial EGMs is less than that of ventricular EGMs. Thus, atrial signals are discriminated by estimating that their dominant frequency does not exceed that of ventricular events. The relative amplitude of the signal associated with an event is computed as the ratio of its amplitude on the high-pass filtered Diagnostic EGM channel divided by its amplitude on the baseline Diagnostic EGM.

A non-ventricular event on the Diagnostic EGM is classified as an atrial event and excluded from analysis if its relative amplitude does not exceed the relative amplitude of ventricular events by more than a certain percentage, such as 5%. They may also be discriminated by other methods such as occurring within a predetermined timing window in relation to the Reference EGM. Optionally, in patients with dual-chamber or triple-chamber (cardiac resynchronization) ICDs, timing of the atrial EGM may be determined from the atrial lead. Optionally, steps 602B, 602C may be omitted for single-coil leads in which the Diagnostic EGM is the integrated-bipolar EGM, which is unlikely to record atrial signals.

Sensed events on the Diagnostic EGM may be determined to be noncardiac EGMs suggesting a lead anomaly if they fulfill two criteria, and possibly, a third optional criteria 603. First, they are neither atrial nor ventricular. Second, they are sufficiently frequent, for example, three events in a rolling window of 20 consecutive ventricular events as determined by the Reference EGM. Third, and optionally, they have sufficient amplitude (e.g. >1 mV). This third optional criterion may be used to exclude diaphragmatic myopotentials (FIG. 8B, reference number 810) that are recorded when the integrated-bipolar EGM is used as Diagnostic EGM on single-coil leads.

Figure 9A:
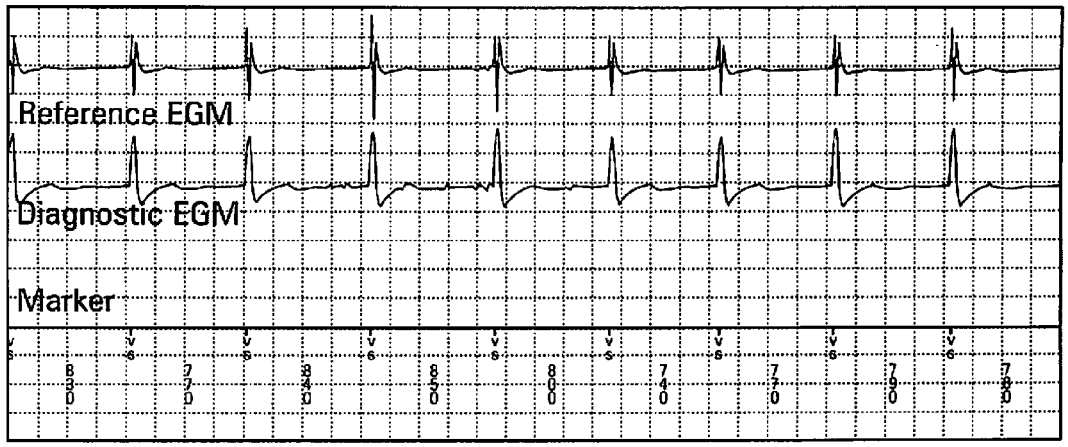
FIGS. 9a-9c depict the signals used in the analysis for a true-bipolar, dual-coil lead.
Figure 9B:
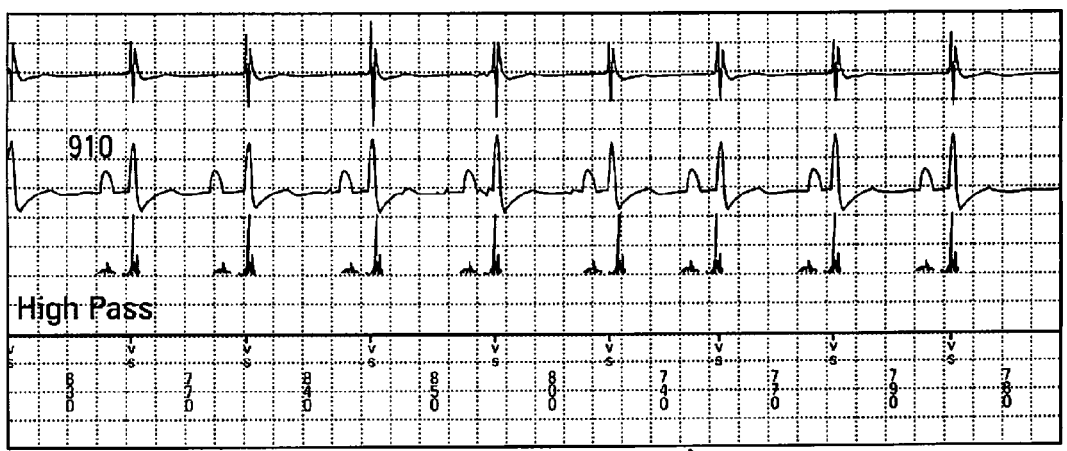
Figure 9C:
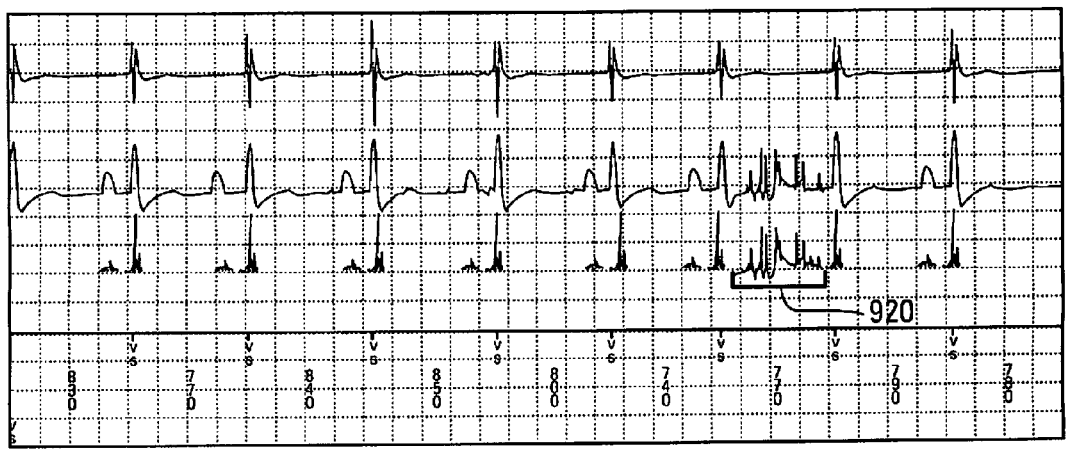

FIGS. 9a, 9b, and 9c depict the signals used in an embodiment of the analysis of 602 and 603 for a true-bipolar, dual-coil lead. Each figure shows a Reference EGM (Tip-Ring, upper tracing) and Diagnostic EGM (Coil-Coil, middle tracing) and Reference EGM marker channel. FIGS. 9b and 9c also show the high-pass filtered and rectified Diagnostic EGM. FIG. 9a shows simultaneous ventricular EGMs on both channels, without atrial or noncardiac signals. FIG. 9b shows atrial signals 910 prior to each ventricular EGM. FIG. 9c shows additional high-frequency signals identified as noncardiac in origin 920.

If too few noncardiac events are recorded after step 603 is completed for a sliding window, monitoring is continued in step 602 and the method loops between these two steps. Optionally, at intervals the method may loop back from 603 to 601.

If sufficient noncardiac events are recorded in 603, then 604 is activated in dual-coil leads. Programming is changed for a limited period of time (e.g. one hour) to monitor three EGMs, the Reference EGM and two secondary, Differential Diagnostic EGMs. The purpose is to isolate the source of the noncardiac signals to either the RV Coil or the SVC Coil. To achieve this, Differential Diagnostic EGMs are recorded between one shock EGM and one pace-sense EGM. In this example, two Differential Diagnostic EGMs are selected, the EGM between the tip electrode and SVC Coil (Tip-SVC Coil) and the integrated-bipolar, Tip-RV Coil EGM. However, it is understood that other pace-sense electrodes could be substituted for the tip electrode including the RV ring electrode or a left-ventricular electrode. The Tip-SVC Coil EGM is not used in any presently available ICD.

Differential Diagnostic EGMs are monitored and processed 605 using substeps 605A-605C, identical to those used for the Diagnostic EGM in steps 602A-602C. Optionally, Steps 605B and 605C may be considered especially important for the Tip-SVC Coil EGM, which is likely to record atrial signals. Optionally, Steps 605B and 605C may be omitted for the integrated-bipolar EGM, Tip-RV Coil EGM, which is unlikely to record atrial signals.

Analogous to 603, it is then determined if noncardiac events are recorded on one or both of the Differential Diagnostic EGMs to determine the source of noncardiac signals 606. There are four possible outcomes of 606: If noncardiac events are not recorded in the allotted time period (an hour in this example), the monitored EGMs are reset to the Reference EGM, the Diagnostic EGM, and any third operator-programmed EGM 607.

Figure 10A:
FIGS. 10a-10c depict possible signals recorded of non-cardiac signals.
Figure 10B:
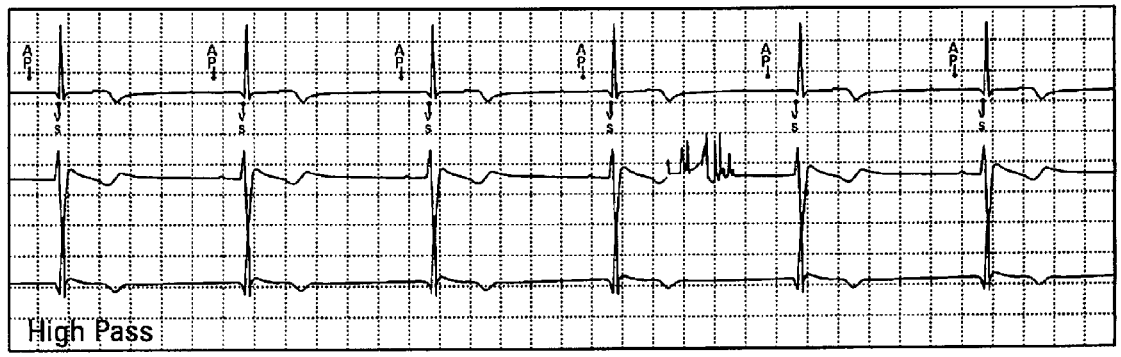
Figure 10C:
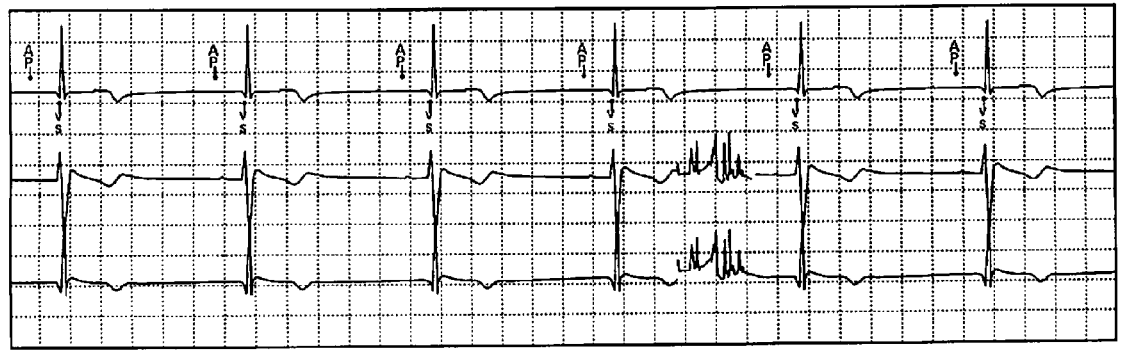

The three remaining possible outcomes are: noncardiac EGMs are recorded only on the Tip-RV Coil EGM 608A, only on the Tip-SVC Coil EGM 608B, or on both 608C. The interpretation of these findings is as follows. If sufficient noncardiac events are recorded only on the Tip-RV Coil EGM (FIG. 10A), the presumed diagnosis is either an in-pocket abrasion of CAN to the conductor of the RV Coil or alternatively abrasion of one of the pace-sense conductors (most likely the cable to ring electrode) against the RV Coil or its conductor. If noncardiac events are recorded only on the Tip-SVC Coil EGM (FIG. 10B), the presumed diagnosis is an in-pocket abrasion of the CAN to the conductor of the SVC Coil or alternatively abrasion of one of the pace-sense conductors against the SVC Coil or its conductor. If non-cardiac events are recorded on both Differential Diagnostic EGMs (FIG. 10C), the potential diagnoses include: abrasion of the RV Coil conductor against the SVC Coil, abrasion of the two conductors against each other (either lead-lead abrasion in the pocket or internal abrasion within the lead), or electromagnetic interference. Optionally, the Diagnostic EGM and Differential Diagnostic EGMs can be filtered to avoid sensing line current at 60 Hz or 50 Hz, depending on the country.

609A and 609B detail the response to findings in 608A, 608B and 608C for dual-coil leads to remove the shorted electrode from the circuit. If noncardiac signals are recorded only on the Tip-RV Coil Differential Diagnostic EGM, the CAN is removed from the defibrillation circuit 609A; and the shock is delivered from RV Coil to CAN. The rationale is that the signals did not enter the Diagnostic EGM from the SVC Coil in 602. So, the signals must have entered from the RV high-voltage components. If the signals entered as a result of an in-pocket, lead-CAN abrasion involving the conductor to the RV coil, excluding the CAN will prevent a shorted shock. If the noncardiac signals are recorded on both Differential Diagnostic EGMs, the SVC Coil is removed from the circuit 609B; and the shock is delivered from RV Coil to SVC Coil. The rationale is that such signals indicate shorting between SVC and RV components within the lead. If noncardiac signals are recorded only from the Tip-SVC Differential Diagnostic EGM, the SVC Coil is also removed from the circuit 609B. The rationale is that the SVC coil is rarely critical, and a short within the lead might manifest itself only on the SVC coil.

In 610, the ICD initiates both a patient alert (e.g. vibratory or audible) and a remote-monitoring alert (providing that the remote internet-based monitoring is enabled) using methods well known in the art.

Optionally, an electrode may be removed from the defibrillation pathway only if the diagnosis may be confirmed by one of several methods. One such method—discussed in "Background" and elucidated in the second embodiment below—includes measurement of impedance using a "sliver" pulse as described in U.S. patent application Ser.

No. 13/843,145 of Swerdlow and Kroll, filed Mar. 15, 2013, the disclosure of which is incorporated by reference in its entirety.

Figure 7:
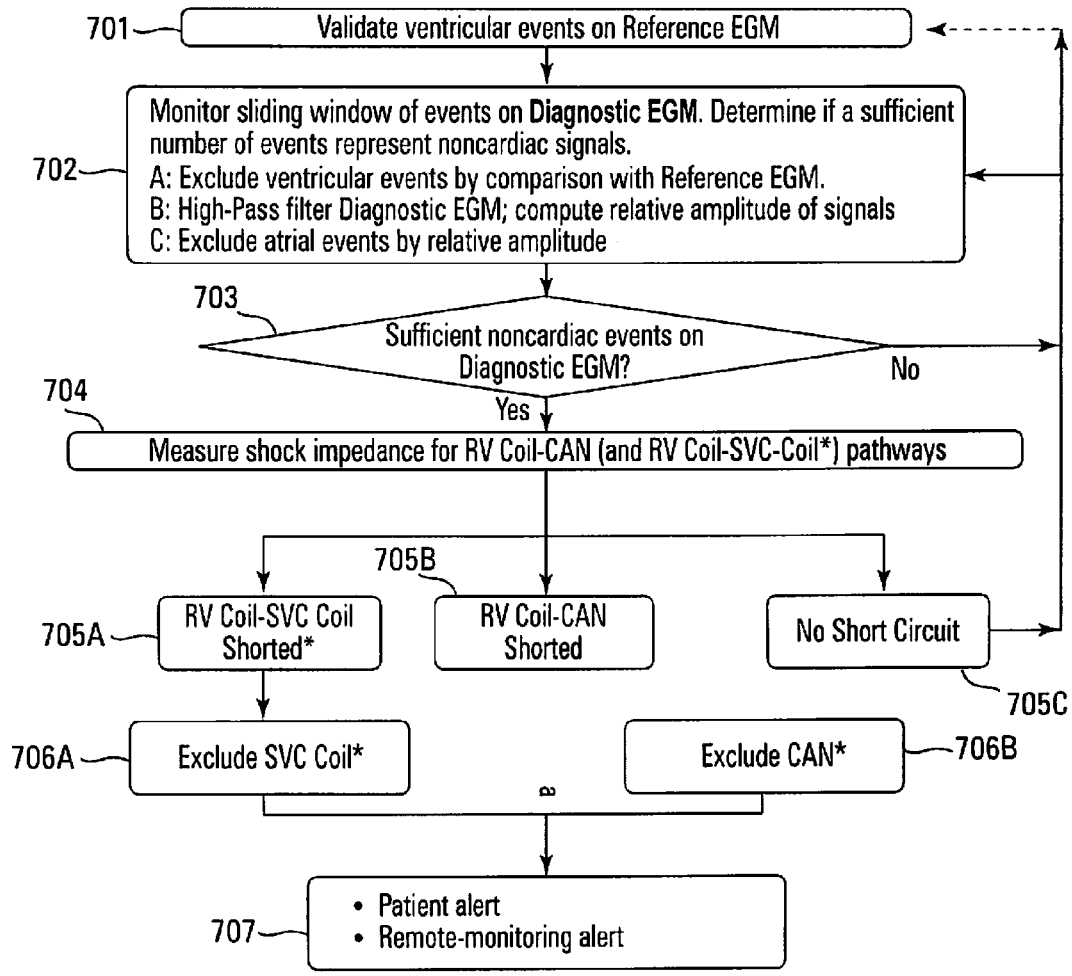
FIG. 7 is a flowchart depicting another embodiment of detecting a short for either dual-coil or single-coil leads.

FIG. 7 is a flowchart depicting a second embodiment applicable to both single-coil and dual-coil leads. Steps 701-703 are identical to those of the first embodiment. In optional 704, shock impedance is measured to detect insulation breaches for each possible two-electrode shock pathway, using one of several advanced methods beyond the presently used low-voltage (painless) measuring technique to estimate shock impedance. One such method is the high-voltage, short-duration "sliver" pulse described in U.S. patent application Ser. No. 13/843,145 that provides an accurate measure of impedance for high-voltage therapeutic shocks. Because such sliver pulses may require considerable battery energy and may be sensed by the patient, it is preferable to deliver them only when there is a high suspicion of lead anomaly. In this embodiment, the sliver pulse method is applied to the RV Coil-CAN pathway in single-coil leads and to both the RV Coil-CAN and the RV Coil-SVC pathways separately in dual-coil leads. A determination is then made if a pathway is shorted based on the method for measuring shock impedance 705A, 705B or if no short circuit 705C is present. This last condition corresponds to a false-positive result from EGM analysis. Thus, by identifying EGMs that likely indicate a lead anomaly involving high-voltage components, embodiments of the present invention can be utilized to set conditions to trigger the sliver pulse analysis.

Optional step 705 applies only to dual-coil leads. If the RV Coil-SVC pathway is shorted, the SVC coil is excluded from the shock pathway 706A, and the shock is delivered from RV Coil to CAN. If the RV Coil-CAN pathway is shorted, the CAN is excluded 706B and the shock is delivered RV Coil to SVC Coil.

Step 707 corresponds to 610 of the first embodiment. The ICD initiates both a patient alert (e.g. vibratory or audible) and a remote-monitoring alert (providing that the remote internet-based monitoring is enabled) using methods known in the art.

Various embodiments of systems, devices, and methods have been described herein. These embodiments are given only by way of example and are not intended to limit the scope of the present invention. It should be appreciated, moreover, that the various features of the embodiments that have been described may be combined in various ways to produce numerous additional embodiments. Moreover, while various materials, dimensions, shapes, implantation locations, etc. have been described for use with disclosed embodiments, others besides those disclosed may be utilized without exceeding the scope of the invention.

The invention claimed is:

1. An automated method of diagnosing an anomaly in an implantable lead of an implantable cardioverter defibrillator (ICD) attached to a dual-coil, true-bipolar defibrillation lead that includes sensing conductors connected to tip electrode and a ring electrode and defibrillation conductors connected to a first coil electrode and a second coil electrode, comprising:

monitoring electrogram (EGM) signals from a Reference EGM defined by a pathway between the tip electrode to the ring electrode through the sensing conductors in the implantable lead and a Diagnostic EGM defined by a pathway between the first coil electrode and the second coil electrode through defibrillation conductors in the implantable lead;

automatically determining valid ventricular events in the Reference EGM;

automatically comparing the Diagnostic EGM with the Reference EGM to determine if noncardiac signals other than valid ventricular events are present on the Diagnostic EGM; and when the noncardiac signals other than valid ventricular events are present:

analyzing EGM signals from at least one Differential Diagnostic EGM defined by a pathway between at least one of the first coil electrode and second coil electrode and at least one of the tip electrode and the ring electrode to determine an electrode responsible for the noncardiac signals;

determining if the electrode responsible for the noncardiac signals is a nonessential coil electrode that should be excluded from a defibrillation pathway to prevent shorting during a therapeutic shock; and when the electrode responsible for the noncardiac signals is a nonessential coil electrode automatically initiating one or more responses selected from the group consisting of:

excluding the nonessential coil electrode from the defibrillation pathway, initiating one or more additional diagnostic tests to confirm that the electrode responsible for the noncardiac signals shorts the defibrillation pathway, initiating a patient alert, and initiating a remote-monitoring alert.

2. The method of claim 1 wherein the Diagnostic EGM is recorded between the Right Ventricular Coil and Superior Vena Cava Coil (Coil-Coil Diagnostic EGM).

3. The method of claim 1 wherein the at least one Differential Diagnostic EGM is selected from the group consisting of: the EGM between the tip electrode and Superior Vena Cava Coil (Tip-SVC Coil), the integrated-bipolar EGM, and the EGM between the tip electrode and Right Ventricular Coil (Tip-RV Coil).

4. The method of claim 1 wherein:

the implantable lead is a true-bipolar lead and the Reference EGM is a true-bipolar sensing EGM (Right Ventricular Tip-Right Ventricular Coil EGM); and the implantable lead is an integrated-bipolar lead and the Reference EGM is a Tip-CAN EGM.

5. The method of claim 1 wherein at least one of the one or more additional diagnostic tests includes delivery of one or more high-voltage, short-duration, sliver pulses.

6. The method of claim 1, wherein the nonessential electrode is the Superior Vena Cava Coil, and therapeutic shocks are delivered between Right Ventricular Coil and CAN.

7. The method of claim 1 wherein the nonessential electrode is the CAN, and therapeutic shocks are delivered between Right Ventricular Coil and Superior Vena Cava Coil.

* * * * *